United States Patent [19]

Gochenouer

[11] Patent Number: 5,028,429
[45] Date of Patent: Jul. 2, 1991

[54] LEG BLISTER

[76] Inventor: Charles J. Gochenouer, 17624 Snohomish Ave., Snohomish, Wash. 98290

[21] Appl. No.: 576,180
[22] Filed: Aug. 30, 1990

Related U.S. Application Data

[63] Continuation of Ser. No. 298,781, Jan. 17, 1989, abandoned, which is a continuation-in-part of Ser. No. 872,153, Jun. 9, 1986, abandoned.

[51] Int. Cl.$^5$ ..................... A61K 35/78; A61K 33/28
[52] U.S. Cl. ............................. 424/195.100; 424/645
[58] Field of Search .............................. 424/195.1, 645

[56] References Cited

U.S. PATENT DOCUMENTS

| | | | |
|---|---|---|---|
| 316,932 | 5/1885 | Baker | 424/195.1 |
| 4,020,153 | 4/1977 | Rowsell et al. | 424/49 |
| 4,032,669 | 6/1977 | Rowsell et al. | 514/708 |
| 4,034,109 | 7/1977 | Rowsell et al. | 514/546 |
| 4,070,419 | 1/1978 | Rowsell et al. | 424/45 |
| 4,070,496 | 1/1978 | Rowsell et al. | 424/45 |

Primary Examiner—John W. Rollins

[57] ABSTRACT

This invention relates to a method of making a chemical composition, the formula for the chemical composition, and the method of applying the chemical composition to animals, specifically horses. The chemical composition uses isopropyl alcohol, mecuric chloride, chlorophyll, comfrey and peppermint. Dye can be added to the chemical composition.

The method of making the chemical composition includes dissolving the comfrey in the isopropyl alcohol, filtering, and then sequentially adding mecuric chloride, chlorophyll, and peppermint. If desired, dye is added after the peppermint.

The method of applying the chemical composition to an animal includes the sedation of the animal, brushing the area to be treated with the chemical composition two times with the second time 12 hours after the first application, keeping the animal dry, and exercising the animal 24 hours after the application.

4 Claims, No Drawings

LEG BLISTER

BACKGROUND OF THE INVENTION

This is a continuation of application Ser. No. 298,781, filed on Jan. 17, 1989, now abandoned, which is a continuation-in-part of application Ser. No. 872,153 filed on June 9, 1986, now abandoned.

1. Field of the invention.

This invention involves the method of making a chemical composition, the chemical composition itself, and the method of applying the chemical composition to an animal, specifically a horse. The chemical composition is commonly known as a leg blister or leg paint.

2. Description of the prior art.

It is known in the prior art that certain chemical formulations, such as leg paints or leg blisters, are a means of treatment of horse injuries. See, for example, the Horseman's Journal, December 1985, pages 50 and 51. Bichloride of mercury and alcohol are commonly known as ingredients in blisters and leg paints. Comfrey is used in the chemical compositions of Hirosaki U.S. Pat. No. 4,059,695 for animal and human treatment, and of Spies U.S. Pat. No. 4,258,035 for dog arthritis. Comfrey is also used in cosmetic compositions of Grollier U.S. Pat. No. 4,459,285.

The primary problem of the known leg paints and leg blisters is the length of time the horse must be treated. The chemical composition, when properly prepared and properly applied, allows the horse to return to training twenty-four hours after first application.

SUMMARY OF THE INVENTION

The subject invention relates to a chemical composition which provides easy and quick treatment of various horse injuries and ailments. In order to produce the chemical composition, a certain method of making the chemical composition must be followed. Additionally, a specified method of applying the chemical composition to the animal must be specifically followed for effective treatment.

The chemical composition uses as the basic ingredient, isopropyl alcohol in the range of by percentage weight 75% to 98%. Mecuric chloride, an irritant ranges from a low of 2% by weight to a high of 25% by weight. The chlorophyll, comfrey and peppermint are used in specific trace amounts. A dye may be added as desired.

In order to develop the chemical composition, a certain method must be followed in combining the constituent chemicals. The initial step requires the placement of comfrey into the isopropyl alcohol for a period of 24 hours. This allows for the maximum absorption of comfrey into the isopropyl alcohol. The isopropyl alcohol-comfrey solution is then filtered. While stirring the isopropyl-comfrey solution, the mecuric chloride is added, the chlorophyll is added, and the peppermint is added, in that order. Green dye may be added after the peppermint if desired.

In order to achieve maximum effectiveness of the chemical composition, certain steps must be followed in applying the chemical composition to the horse. In general, the horse should be sedated for a period of two to four hours. The area to be treated should be brushed with the chemical composition. It is required that the horse and, particularly, the treatment area be kept dry. Twelve hours after applying the first treatment, a second treatment must be applied. Twenty-four hours after the first application, the horse must be exercised.

It is an object to provide a chemical composition for treatment of horses which reduces the amount of treatment time.

It is a further object to provide a readily available method for producing the treatment chemical composition.

It is another object to provide a clear and simple method of application of the treatment chemical composition to the injured horse.

DETAILED DESCRIPTION OF THE PREFERRED EMBODIMENT

Horses, particularly race horses, have been bred over many years to produce a fast horse carrying a human being on its back. This has created severe stress in the horse, particularly in the lower extremities. Race horses suffer frequent ailments which require treatment. The more quickly the horse can be returned to good health, the more quickly the horse can be racing again.

The most common type of injuries are bone chips, spurs, bursitis, and "blood calcium". These various injuries occur to the splint bones, suspensories, shin bones, ring bone, osselets, spavins, sesamoids, spine, shoulders, knees, ankles, hocks, and stiffles. Of course, tendons and muscles are also strained and require treatment.

Testing of animal's draining serum from the sores after application of the blister has shown that the calcium is removed as is shown by the following table:

| Sample #1 | Weight (Serum) | Ca (ppm) | Hg (ppm) |
|---|---|---|---|
| 1 | .07 g | 428 | Appx 0 |
| 2 | .5 g | 250 | 98 |
| 3 (clear) | .96 g | 100 | 46 |
| 3 (solid) | .049 g | 450 | 81 |

One of the concerns is with the use of mercury in the composition and whether or not the mercury within the horse will increase. Results of blood testing before treatment and after treatment in two cases indicate that mercury actually decreased from 0.0048 mg/dl to 0.004 mg/dl. In the second example the mercury decreased at a pretreatment level from 0.0116 mg/dl to 0.0020 ml/dl. Both tests were performed with the blood of the horse.

As surprising result is the ability of the composition to remove toxic elements from the horse. The following table shows a hair sample of a horse before treatment and a hair sample of a horse after treatment. Both the aluminum and magnesium compounds are high in this horse. Notice that after treatment with the hair sample the ranges are normal for the horse.

| Elements | Normal Range (Horse) | Pre-treatment (mg.) | Post-treatment (mg.) |
|---|---|---|---|
| Calcium | 166–202 | 67 | 65 |
| Magnesium | 59–82 | 129.0 | 80.5 |
| Sodium | 35–58 | 20 | 8 |
| Potassium | 35–51 | 29 | 15 |
| Copper | .55–.8 | .8 | .8 |
| Zinc | 8–12 | 11 | 11 |
| Phosphorus | 20–27 | 27 | 11 |
| Iron | 18–34 | 6.4 | 6.5 |
| Manganese | .58–.82 | .29 | .21 |
| Chromium | .07–.13 | .07 | .06 |
| Nickel | .12–.50 | .10 | .1 |
| Selenium | .03–.18 | .06 | .04 |
| Arsenic | 0–0.06 | .01 | .01 |

-continued

| Elements | Normal Range (Horse) | Pre-treatment (mg.) | Post-treatment (mg.) |
| --- | --- | --- | --- |
| Mercury | 0–0.29 | .02 | .24 |
| Cadmium | 0–.19 | .01 | .01 |
| Lead | 0–1.9 | .1 | .1 |
| Aluminum | 0–2.5 | 8.4 | 4.8 |

A blood sample taken after the treatment showed the following results.

| Test | Normal Range | Post-treatment (ppm) |
| --- | --- | --- |
| Calcium | .9–2.1 | .5 |
| Magnesium | 3.0–4.7 | 3.0 |
| Sodium | 54–102 | 65 |
| Potassium | 120–240 | 280 |
| Copper | .04–.12 | .12 |
| Zinc | .64–1.2 | 1.23 |
| Phosphorus | 18–32 | 65 |
| Iron | 56–88 | 60 |
| Manganese | .01 | .01 |
| Chromium | 07–.23 | .04 |
| Nickel | .1 | .1 |
| Selenium | .05 | .05 |
| Arsenic | .05 | .05 |
| Mercury | .05 | .05 |
| Cadmium | .02 | .01 |
| Lead | 0–.05 | .04 |
| Aluminum | 0–.1 | .1 |

With respect to the chemical composition, the isopropyl alcohol can range from a low of 75% by weight to a high of 98% by weight. Mecuric chloride can range from a low of 2% by weight to a high of 25% by weight. Chlorophyll can range from 0.0006% to 0.0025%. Comfrey similarly ranges from a low of 0.0006% to a high of 0.0025%. Peppermint ranges from a low of 0.0006% to a high of 0.0025%. The preferred embodiment uses 91.99625% of isopropyl alcohol, 8% mecuric chloride, 0.00125% chlorophyll, 0.00125% comfrey, and 0.00125% peppermint. The preferred embodiment has been used to affectively treat the various ailments and injuries listed above.

When green dye is used, it simply replaces a similar percent of the isopropyl alcohol. For example, in the preferred embodiment, if 0.05% green dye is used, the isopropyl alcohol reduces to 91.94625% by weight.

The general method of making the chemical composition comprises the following steps:

1. Comfrey is dissolved into isopropyl alcohol for a period of 24 hours.
2. The solution of isopropyl alcohol and comfrey is filtered.
3. The isopropyl-comfrey solution is stirred or blended while the mecuric chloride is added.
4. Chlorophyll is added after the mecuric chloride.
5. Peppermint is added after the chlorophyll.
6. The stirring or blending is done for five to 15 minutes.
7. Green dye is added if desired.

The method used when applying the chemical composition for treatment to a horse comprises the following steps:

1. For legs, clip the hair six inches above the knee down to the cornet. For areas other than the legs, don't clip the hair. Note that the treatment must be applied in pairs, i.e., this means that both rear legs or both front legs, or stifles of the horse must be treated.
2. Sedate horse sufficiently for a total of two to four hours.
3. Apply the chemical composition to the horse in the area to be treated with a brush or sponge. Cover the entire circumference of the leg when treating the leg except the excessory carpel bone, the face of the hock and the cap of the hock.
4. Horse must be kept in a dry area.
5. Repeat application of the chemical composition to the horse after 12 hours.
6. After 24 hours, the horse must be exercised.

The horse should swell where the problem areas occur. After 24 hours, the horse may be draining a serum from the swollen areas.

It will be understood that the specifications and examples herein are merely illustrative and not limiting of the present inventions and that other embodiments within the spirit and scope of the invention will suggest themselves to those skilled in the art.

What is claimed is:

1. A chemical composition for topical application for animal injuries primarily related to bone injuries and removal of toxic elements comprising:
   a 75% to 98% isopropyl alcohol;
   b 2% to 25% mecuric chloride;
   c 0.0006% to 0.0025% chlorophyll;
   d 0.0006% to 0.0025% comfrey; and
   e 0.0006% to 0.0025% peppermint.

2. A chemical composition for topical application for animal injuries primarily related to bone injuries and removal of toxic elements comprising:
   a 91.99625% isopropyl alcohol;
   b 8% mecuric chloride;
   c 0.00125% chlorophyll;
   d 0.00125% comfrey; and
   e 0.00125% peppermint.

3. The method of producing the chemical composition of claim 1 for topical application for animal injuries primarily related to bone injuries and removal of toxic elements comprising the following steps:
   a Dissolve comfrey into isopropyl alcohol for 24 hours;
   b Filter the solution of isopropyl alcohol and comfrey;
   c Stir the isopropyl—comfrey solution while adding the mecuric chloride;
   d Continue stirring the solution while adding the chlorophyll;
   e Continue stirring the solution while adding peppermint; and
   f Stop stirring after five to fifteen minutes.

4. The method of using a chemical composition of 75% to 98% isopropyl alcohol; 2% to 25% mecuric chloride; 0.0006% to 0.0025% chlorophyll: 0.0006% to 0.0025% comfrey; and 0.0006% to 0.0025% peppermint for topical application for injuries to horses primarily related to bone injuries comprising the following steps:
   a Clip the hair on the horse's legs to be treated from six inches above the knee down to the cornet on the legs to be treated;
   b Sedate horse sufficiently for a total of two to four hours;
   c Apply the chemical composition to the horse in the area to be treated with a brush or sponge, but cover the entire circumference of legs treated except excessory carpel bone and face of the hock;
   d Keep horse in a dry area;
   e Repeat application of the chemical composition to the horse after 12 hours; and
   f Exercise the horse after 24 hours.

* * * * *